United States Patent
Dayn

(10) Patent No.: US 6,245,565 B1
(45) Date of Patent: *Jun. 12, 2001

(54) RECOMBINASE MEDIATED DNA MODIFICATIONS

(76) Inventor: Andrey Dayn, 580 Arastradero Rd., #308, Palo Alto, CA (US) 94306

( * ) Notice: Subject to any disclaimer, the term of this patent is extended or adjusted under 35 U.S.C. 154(b) by 0 days.

This patent is subject to a terminal disclaimer.

(21) Appl. No.: 09/301,153

(22) Filed: Apr. 28, 1999

Related U.S. Application Data

(63) Continuation of application No. 08/882,756, filed on Jun. 26, 1997, now Pat. No. 5,929,043, which is a continuation of application No. 08/381,634, filed on Jan. 31, 1995, now abandoned.

(51) Int. Cl.$^7$ ........................................ C12N 5/02
(52) U.S. Cl. ..................... 435/375; 475/194; 536/23.5
(58) Field of Search ..................... 435/440, 375, 435/194; 536/23.5; 514/44

(56) References Cited

U.S. PATENT DOCUMENTS 5,264,618   11/1993   Felgner et al. ..................... 560/224
5,273,881   12/1993   Sena et al. ..................... 435/6

FOREIGN PATENT DOCUMENTS

93/05178   3/1993   (WO).

OTHER PUBLICATIONS

Revet et al., "Homologous DNA Targeting with RecA Protein–Coated Short DNA Probes and Electron Microscope Mapping on Linear Duplex Molecules, " *J. Mol. Biol.*, 232:779–791 (1993).

Sena et al., "Targeting in Linear DNA Duplexes with Two Complementary Probe Strands for Hybrid Stability," *Nature Genetics*, 3:365–372 (Apr. 1993).

*Primary Examiner*—James Ketter
(74) *Attorney, Agent, or Firm*—Flehr Hohbach Test Albritton & Herbert LLP

(57) ABSTRACT

Nucleoproteins comprising overlapping homologous DNA sequences coated with a recombinase are employed for introduction into cells to produce double D-loop structures. The sequences may be modified with various moieties which result in modification of DNA. Formation of the D-loops results in inhibition of replication and transcription, where the moieties can be employed for permanent scission or modification of the DNA. The methods and compositions can be used for investigating physiological processes, for producing animal models, and for inhibition of an undesirable phenotype in vivo.

14 Claims, No Drawings

RECOMBINASE MEDIATED DNA MODIFICATIONS

This application is a continuation of Ser. No. 08/882,756 filed Jun. 26, 1997, now U.S. Pat. No. 5,929,043 which is a continuation of Ser. No. 08/381,634 filed Jan. 31, 1995, now abandoned.

INTRODUCTION

1. Technical Field

The field of this invention is the inactivation of target DNA in vivo.

2. Background

The ability to selectively inhibit the growth of a subset of cells in a mixture of cells has many applications in culture and in vivo. Where two sets of cells have distinguishing characteristics, such as tumor cells which require expression of one or more genes, which are not expressed in normal cells or only expressed at a low level, there is substantial interest in being able to selectively inhibit the proliferation of the tumor cells. Where groups of cells are differentiating, and at one level of differentiation, expression of a particular gene is required, the ability to inhibit the expression of that gene can be of interest. Where cells are infected by viruses, parasite or mycoplasmas, the selective ability to inhibit the growth of the virus or mycoplasma can be an important goal.

In the studies of metabolic processes, differentiation, activation, and the like, there are many situations where it is desirable to be able to selectively inhibit the transcription of a particular gene. In this way, one can study the effect of a reduction in the transcription of the gene and expression of the gene on the phenotype of the cell. In the extensive efforts to understand embryonic and fetal development, to define segmental polarity genes and their function, there is also interest in being able to selectively inhibit particular genes during various phases of the development of the fetus.

As in the case of the studies in culture, selective inhibition of particular genes can also be of interest in vivo. In many situations, cellular proliferation can be injurious to the host. The proliferation can be as a result of neoplasia, inflammation, or other process where increased number of cells has an adverse effect upon the health of the host.

There is, therefore, substantial interest in finding techniques and reagents which allow for selective inhibition of particular genes, so as to control intracellular molecular processes.

Relevant Literature

WO93/05178 provides an extensive description of double D-loop formation, with an extended bibliography of references. Sena and Zarling, (1993) Nature Genetics 3:365–372 and Révet, Sena and Zarling, J. Mol. Biol. 232:779–791 describe double D-loop formation. Golub et al., (1992) Nucleic Acids Res. 20:3121–5; Golub et al., (1993) Proc. Natl. Acad. Sci. USA. 90:7186–90; Ferrin and Camerini-Otero, (1991) Science 254:1494–7.; Koob et al. (1992) Nucleic Acids Res. 20:5831–6; Revet et al. (1993) J. Mol. Biol. 232:779–91; Sena (1993) Nature Genetics 3:365–371 and Jayasena and Jonnston (1993) J. Molec Biol. 230:1015–1024.

SUMMARY OF THE INVENTION

Recombinase coated pairs of single-stranded probes having a region of complementarity are introduced into cells. One or both probes may be modified with an agent capable of inhibiting transcription. The pairs of recombinase coated probes are introduced into cells, where the probes are directed to a DNA target sequence, particularly genes, primarily directed to the 5'-transcriptional initiation region or other essential transcriptional initiation sequence, such as an enhancer. The formation of the double D-loop inhibits copying, e.g. transcription, and by providing for a DNA modifying agent bound to one or both of the probes, further inhibition can be achieved.

DESCRIPTION OF THE SPECIFIC EMBODIMENTS

Methods and compositions are provided for inhibiting copying of a DNA sequence, where copying intends transcription and replication. Of particular interest is selectively inhibiting the transcription of at least one gene in a cellular host. The method comprises introducing a pair of probes having a complementary region, where the pair of probes is coated with a recombinase. One or both of the probes may be further modified with an agent which can react with DNA to further inhibit copying. The probes are introduced into the cells by any convenient means, in culture or in vivo. As a result of the introduction of the probes into the cell, with formation of double D-loops, copying of the target DNA is substantially diminished, resulting in a change in the phenotype of the cells or mortality. The subject compositions may be used by themselves or in conjunction with other agents, depending upon the purpose for which the subject compositions are employed.

The probes may be any sequences which have substantial homology with each other and with a target DNA sequence. Usually the homology between the two probes and the target sequence will be at least about 70% between target and probe, more usually at least about 90% and preferably 100% (complementarity). By homology is intended sequences having substantial identity and the percent homology is defined in accordance with FASTP (Pearson and Lipman, Proc. Natl. Acad. Sci. USA 85, 2444–8 (1988).

For the most part, the DNA sequences will be the naturally occurring nucleotides, although some modifications may be made, where a proportion of the nucleotides may be modified to enhance stability. Thus, various oxygens of the phosphate in the backbone may be substituted with sulfur, nitrogen or carbon (methylene), or an unnatural sugar may be employed, e.g. replacing ribose with arabinose. To enhance stability, one or both termini of the sequence may be modified, particularly by functionalization. The modification may serve to inhibit exonuclease, to link to another moiety, or the like. Thus, ethers, amino groups, esters, or other functionality may be provided at one or both termini. Reactive moieties which affect the ability for copying may include single stranded or double stranded DNA scission inducing molecules, intercalating molecules, cross linking molecules, photoactive molecules, and the like. Scission inducing molecules provide for cleavage of one or both of the DNA strands of the target sequence. These may include chelated metal ions, such as iron and copper. Chelating agents may include ethylenediamine tetraacetic acid (EDTA), nitrilo triacetic acid (NTA), 2,9-dimethyl-1,10-phenanthroline, etc. Alternative molecules may include electron accepting molecules, such as quinones, and the like.

Depending upon the particular purpose of the subject composition, various agents which provide for cross linking may be employed. Photoactivatable cross linkers include coumarin, psoralen, and other commercial cross-linking molecules available from Pierce and Pharmacia. Other compounds include oxetanes, or other unstable dioxacyclic compounds.

A large variety of intercalating agents are known, including many dyes, such as thiazole orange, ethidium bromide, phenanthridines, actinomycin D, etc. By intercalating into the DNA, these molecules will further stabilize the complex and reactivity and if chemically modified can interact with the DNA strands to form covalent bonds.

In addition, one can provide for compounds which are activated intracellularly to react with nucleotides. These compounds include quinones having various substituents.

The various active moieties may be tethered to the DNA sequence by a bond or any convenient linking group, which may be a single atom or a chain of about fifty atoms, where the atoms may include carbon, nitrogen, oxygen, sulfur, phosphorous, and the like. Thus, the chain may be an oligonucleotide chain, peptide nucleic acid chain (nucleic acid chain, where phosphate is substituted with glycine), oligosaccharide, polyoxyalkylene, polyamide, e.g. polypeptide, alkylene, arylene, combinations thereof, or the like. The particular linking group is not critical, but one may be selected over another for synthetic convenience, in relation to the particular moiety, to provide solubility, flexibility, hydrophobicity, enhanced binding to DNA, or to remove secondary structure. Usually, there will be from 0 to 3 active moieties per probe, more usually from 0 to 2, particularly 0 to 2 for the combination of probes, more usually 0 to 1 for the combination of probes. The size of the probes, extent of homology, and areas of non-homology may vary widely. Thus, one may employ combinations of partially overlapping probes which alternate where the first pair has the 3' portion of one probe overlapping with the 5' portion of the other probe followed by the 3'portion available in the first pair of probes overlapping with the 5' portion of the next probe and so on. Alternatively, one could have one long probe and three smaller homologous probes. One could have a single pair of probes or a combination of two or more pairs of probes. The ssDNA probes may also be used, where the probes are conveniently proximal to the termini of linear ssDNA, where the termini will be at least partially overlapping when hybridized to the target or contiguous when bound to the target. In effect, a single probe may be divided into two regions, which when the two regions are bound to the target sequence, the probes will be substantially contiguous, e.g. spaced apart by fewer than about 3 nucleotides. Thus one could have a single molecule comprising the two probes or two molecules, where the termini of the two molecules comprise a sequence which is complementary to the termini of a second molecule and homologous to one strand of the target sequence. The probes or regions may be linked at either of their termini, preferably the 5' terminus of one being linked to the 3' terminus of the other, so as to form a circle when bound to the target, so that the 3' terminal nucleotide of one region is contiguous to the 5' terminal nucleotide of the other region in the 5'-3' direction of the ssDNA. Where the termini are contiguous when bound to the target sequence, the ends may be subject to joining, including ligation, to prevent removal from the target sequence. For joining chemically, one or both of the contiguous ends may be modified to provide an agent capable of chemical linkage.

The particular choice will depend upon the target sequence, the difference between the target sequences and other sequences in the host, the desired stability of the D-loop, whether other moieties are present for stabilization, the particular target, and the like. There will be a combination of at least 2 probes having at least 30 nucleotide overlaps with at least 70% homology, usually at least 50 nucleotide overlap, preferably at least about 75 nucleotide overlap or greater. The probes will be at least 30 nucleotides, preferably at least 50 nucleotides, more preferably at least 100 nucleotides, and may be 1000 nucleotides or greater, usually being not more than about 500 nucleotides.

For the purposes of this invention, recombinases will be recA-like proteins. These proteins may be characterized by forming a filament with ssDNA, induces strand exchange in providing natural strand displacement by the incoming strand, and is normally associated with DNA repair. In the subject invention, the recombinase may be any protein which enhances the formation of the D-loops, by itself or in conjunction with other subunits of a recombinase complex. Various naturally occurring or mutant recombinases are available, particularly recA from *E. coli*, e.g. recA-803,Rad 51 and Rad 52, from *S. cerevisiae*, Rad51 like, DMC1, mei3 from *N. crassa*, human recombinase from human cells, and the like. See particularly page 15, lines 10–30 of WO93/05178. The ratio of the recombinase to the nucleotides of the probe will generally be in the range of about 1:3–50, more usually 1:3–25, depending upon the size of the probe, the smaller probes requiring higher levels of recombinase. The probes can be synthesized in accordance with conventional techniques, either manually or by automated synthesizers. By appropriate choice of the terminal nucleotide, the terminal nucleotide may be functionalized, so as to be resistant to exonuclease, provide for a site for linkage of the DNA deactivating moiety, and the like. For automated synthesizers, usually a 3' terminus will be linked by a cleavable functionality to a bead. This functionality may be employed to serve as the 3' terminus and may also serve as a site for linkage of the DNA deactivating moiety. The particular manner in which the subject probes are synthesized is not critical to this invention.

For coating the probes with the recombinase to produce the nucleoprotein filament probe, one combines single-stranded DNA with the recombinase in an appropriate buffered medium in the presence of a cofactor and magnesium ion. A variety of cofactors may be employed, such as ATPγS, rATP, dATP, GTPγS, or equivalent molecules, mixtures thereof, and the like. The ratio of the recombinase per nucleotide of the probe will generally range from about 1–50:1 usually in the range of 2–6:1 more usually in the range of 2–4:1. Thus, a high concentration of recombinase and cofactor may be employed to provide for a substantially complete coating of the probe and to prevent reannealing of the ssDNA probes. Alternatively, lower amounts of the recombinase may be employed where a lower ratio of recombinase to nucleotide will suffice. Generally, the cofactor will be in the range of about 0.2–12 mM, preferably about 2.4–8 mM. The magnesium ion will generally range from about 4–25 mM, more usually 6–8 mM, and may be conveniently present as the acetate. The probe may then be isolated and purified by any convenient means. Conveniently, the probes may be isolated by filtration, where the filter will retain the recombinase coated probes, while allowing individual molecules to pass through the filter, by gravity sedimentation, centrifugation, or the like. The probes may then be stored for use, particularly cold or frozen, where the pairs of probes may be combined and retained in the same container. Conveniently, the probes may be lyophilized and maintained as a dry powder, being reconstituted when needed.

For the most part, the subject invention will be used with a gene as the target sequence. However, the probes may be directed against any target sequence associated with replication, such as a centromere, telomere, replication origin, or the like, repetitive sequences, etc. For target genes, the probes may be complementary to any gene of interest (including the 5' transcription regulatory region, which includes the 5' untransalated region, the coding region, and the transcriptional termination region), particularly the sequences associated with transcription initiation, which include the TATA box, CAAT sequence, the associated regions, enhancers, or other sequence essential to transcription. Therefore, the sequences specific for particular transcription factors will also provide for targets. Alternatively, the sequences may be present in the coding region, at splice sites, or the like. Combinations of probes may be employed, where the probes are directed both to transcriptional elements and to coding sequences. Since in each instance, one will achieve varying degrees of inhibition of transcription and expression, for each target, one may optimize the particular sequence. However, by directing the probes to the TATA-CAAT region, enhancer regions, and transcription factor binding sequences for response elements, one can substantially ensure the substantial inhibition of transcription of the gene.

Genes of interest will be any of a large variety of genes associated with housekeeping, proliferation, differentiation, activation, transcription, oncogenesis, and the like, where the genes will be associated with cellular genes. Alternatively, the genes may be genes associated with pathogens, including microorganism, parasitic and viral genes, where a wide variety of genes may be targets, such as genes associated with transcription factors, polymerases, reverse transcriptases, helicases, topoisomerases, capsid antigens, coat proteins, integrases, and the like.

The particular target can depend upon the particular purpose for which the probe is employed. Targets of interest include oncogenes, transcription factor genes, proliferation repressor genes, mutant tumor suppressor genes, segmental polarization genes, homeobox genes, addressin genes, homing receptor genes, major histocompatibility complex genes, immunoglobulin genes, cytokine genes, immunosuppressive transforming growth factor genes, colony stimulating factor genes, drug pump genes (mdr genes), integrin genes, enzyme genes, cytostructural genes, membrane channel genes, etc. In some instances, one may wish to block the 3' untranslated region (3' UTR), where the 3' UTR is known to have a regulatory function. In this manner, one may determine what functions are regulated by the 3' UTR. Target oncogenes for the treatment of cancer include src, ras, sis, fos, erb, erbb2, neu, myc, gli, etc. Other genes to be inhibited include receptors, such as the EGF receptor, estrogen receptors, PDGF receptor, viral receptors, including CD4 for HIV, and the like.

Also, various specialized proteins may be of interest for inhibition, such as telomerases, in understanding senescence, heat shock proteins, in understanding response to adverse conditions in their activity in helping folding of proteins, recombinases, in understanding processes involved with correction and DNA modification, viral integrases and rep proteins in understanding processes in viral replication and integration, polymerases, in understanding the roles specialized polymerases play, zinc finger DNA binding proteins involved in transcription, and the like.

Pathogenic prokaryotes of interest include Vibrio, e.g. *V. cholerae*; Escherichia, e.g. Enterotoxigenic *E. coli*, Shigella, e.g. *S. dysenteriae*; Salmonella, e.g. *S. typhi*; Mycobacterium e.g. *M. tuberculosis, M. leprae*; Clostridium, e.g. *C. botulinum, C. tetani, C. difficile, C.perfringens*; Cornyebacterium, e.g. *C. diphtheriae*; Streptococcus, *S. pyogenes, S. pneumoniae*; Staphylococcus, e.g. *S. aureus*; Haemophilus, e.g. *H. influenzae*; Neisseria, e.g. *N. meningitidis, N. gonorrhoeae*; Yersinia, e.g. *G. lamblia Y. pestis*, Pseudomonas, e.g. *P. aeruginosa, P. putida*; Chlamydia, e.g. *C. trachomatis*; Bordetella, e.g. *B. pertussis*; Treponema, e.g. *T. palladium*; and the like.

Pathogenic eukaryotes of interest include Cryptococcus, e.g. *C. neoformans*; Candida, e.g. *C. albicans*; Histoplasma, e.g. *H. capsulatum*; Coccidoides, e.g. *C. immitus*; Giardia, e.g.*G. lamblia*; Plasmodium, e.g. *P. falciparum, P. malariae, P. vivax*; Toxoplasma, e.g. *T. gondii*; Leishmania, e.g. *L. mexicana*; and the like.

Viral groups of interest include orthomyxoviruses, e.g. influenza virus; paramyxoviruses, e.g respiratory syncytial virs, mumps virus, measles virus; adenoviruses; rhinoviruses; coronaviruses; reoviruses; togaviruses, e.g. rubella virus; parvoviruses; poxviruses, e.g. variola virus, vaccinia virus; enteroviruses, e.g. poliovirus, coxsackievirus; hepatitis viruses, e.e. hepatitis B virus, hepatitis C virus; herpesviruses, e.g. Herpes simplex virus, varicella-zoster virus, cytomegalovirus, Epstein-Barr virus; rotaviruses; Norwalk viruses; hantavirus; arenavirus, rhabdovirus, e.g. rabies virus; retroviruses, such as HIV, HTLV-I and -II; papovaviruses, e.g. papillomavirus; polyomaviruses; picornaviruses; and the like.

When the subject probes are used in culture, the probes will be introduced into the culture at an effective concentration based on the number of cells to provide the desired level of inhibition. Usually, the ratio of probe to target sequence will be in the range of about 1–30:1, more usually in the range of about 2–25:1. Therefore, the amount of probe which is employed will be dependent upon the number of target sequences present, by virtue of the number of cells, the number of copies of the target sequence, the number of integrated viruses, the number of viral molecules, the number of episomal elements, or the like. The probes are able to cross the membrane barrier and be taken up by the cells, although various techniques can be employed to enhance the efficiency of translocation into the cytoplasm of the cell. For example, one may use liposomes, where the liposome comprises the fusogenic HVJ protein of the Sendai virus or respiratory syncytial virus or gramicidin S peptide. By providing for preparation of the liposomes in the presence of the probes, the probes will be incorporated into the lumen of the liposomes. The liposomes will then fuse with the cellular membrane releasing the probes into the cytoplasm of the cell. Lipofection may be employed using DOTAP (Boehringer Mannheim). Other techniques include electroporation, fusion, microinjection, biolistics, polyamidoamine dendrimer complexes, and the like.

The subject probes may also be used in mammalian hosts. Mammalian hosts include primates, particularly humans, domestic animals, such as bovine, equine, feline, canine, porcine, ovine, lagomorpha, murine, etc. These various hosts may be used for research purposes, for treatment of indications associated with genetic disorders, for the treatment of pathogens, and the like.

The subject compositions may be administered systemically or locally. For many applications, local administration will be preferred. Systemic application will generally involve parenteral application, particularly injection, where the injection may be intravascular, intramuscular, peritoneal, subcutaneous, etc. As indicated above, the subject compositions may be administered without incorporation into a liposome or other vehicle or by incorporation into a liposome. Physiologically acceptable vehicles will be employed, such as water, saline, phosphate buffered saline, ethanol, vegetable oil, etc. The amount of the probes which is employed will vary depending upon the particular target, the manner of administration, the frequency of administration, the stability of the probes, and the like. Generally, amounts which will be employed systemically will provide for a blood concentration in the range of about 1 nM to 10 µM.

For local administration, various techniques may be employed. Particularly, for a region which can be reached with a needle, one may use the subject compositions in conjunction with a matrix which slows the transport of the subject compositions away from the locale at which the subject compositions are introduced, or with a pump which provides for continuous local infusion. Various matrices have been employed, such as collagen, fibrinogen, hyaluronic acid and the like. Generally, the subject compositions will range in from about 0.5 to 70, more usually from about 1 to 35 weight percent of the composition. Other compositions may be present, such as vasoconstrictors, stabilizers, or other agents, depending upon the purpose for which the subject compositions are employed.

For treatment of cancer, the subject compositions may be used in conjunction with cytotoxic agents, where the cytotoxic agents are at or below their normal concentration. Thus, by employing a combination of the subject compositions with cytotoxic agents, the cytotoxic agent can be used at from about 10 to 60% of its normal therapeutic dosage. Cytotoxic agents include cis-plat, vinca alkaloids, 5-fluorouracil, adriamycin, methotrexate, actinomycin D, BCNU, etc.

The subject compositions may be used for inhibiting specific cell lineage development, e.g., NK, LAK, B- and T-cell development, by inhibiting the expression of CD4, CD8, or a member of the CD3 complex. Other proteins associated with activation may also be the subject of inhibition, either individually or in conjunction with the inhibition of other genes. In addition, the subject compositions can be used to inhibit cytokines associated with specific activation, such as IL-2 and IL-4. By inhibiting expression of IL-4, allergic responses can be diminished. The subject compositions may also be employed in producing animal models for a wide variety of diseases associated with genetic defects. Thus, those diseases where the lack of a competent protein results in an adverse phenotype can be studied in animal models, where by employing the subject compositions, expression of the particular protein may be inhibited for an extended period of time. Also, by varying the nature of the sequence, as to its terminal groups and degree of homology, the period of time for the inhibition, as well as the level of inhibition, may be modulated, so as to have a model where the phenotype may be reversed. Animal models may be developed associated with the inhibition of expression of apolipoproteins, cytokines, recombinases, proteins associated with differentiation, growth and maturation, such as CD4, CD8, growth factor receptors, interferon receptors, virus receptors, and the like. Particularly, mice and rats may be temporarily or permanently modified as to phenotype, depending upon the nature of the probes, the concentration employed, whether the probes have the ability to permanently modify the DNA, and the like.

The subject compositions can be provided as kits, where the complementary sequences uncoated or pre-coated with the recombinase and comprising the side chain, as appropriate, can be supplied. Thus, at least one pair of probes would be provided, conveniently in a single vessel. other combinations of probes may also be provided, either in the same or different vessels, depending upon the nature of the target. The probes will normally be made available as a dry powder, which can be reconstituted prior to use. When used in vivo, the compositions will be sterilized and maintained in a sterile container prior to use.

The following examples are offered by way of illustration and not by way of limitation.

EXPERIMENTAL

I. Inactivation of c-Ki-ras protooncogene

Two compositions were prepared comprising the sequence immediately downstream of the transcriptional start sites of the c-Ki-ras prcotooncogene. (Hoffman, et al. (1990) Proc. Natl. Acad. Sci. USA 87: 2705–2709; Barbacid (1987) Annu. Rev. Biochem. 86: 779–827).

In the first composition, coumarin is present at the 5' terminus by adding as the last nucleotide 3'-O-(N-disopropylamino) phosphoramidite derivative of 4,4'-dimethoxytrityl derivative at the 5 ' position of the 2'-deoxyriboside of 7-hydroxymethylcoumarin, followed by deprotection of the deoxyriboside. See U.S. Pat. No. 5,082, 934. The coumarin substituted oligonucleotide is then isolated in accordance with conventional ways.

The second composition has an DTPA-Fe chelate attached at the end of the oligonucleotide prepared in accordance with conventional ways. The oligonucleotide was amino linked and coupled to diethylenetriaminepentaacetic acid (DTPA) isothiocyanate as previously described. (Dewanjee et al., Biotechniques 16:844–6 (1994)

The Y1 cell line, established from the mouse adrenocortical tumor LAF, was employed. (Schwab et al. (1983) Nature 303:497–501) Y1 has the c-Ki-ras protooncogene amplified 50 times.

With each of the above compositions, the following studies are carried out:

$10^6$ Y1 cells are seeded in plates the night before transfection in DMEM with 10% FCS and maintained under normal growth conditions. The coated oligonucleotide compositions are prepared by coating the above oligonucleotides with RecA in the presence of 20mM $Mg^2$+and 1 mM ATPγS (5–10 µg of DNA in 50 µl of coating buffer). The RecA coating reaction is performed as follows. DNA probes were coated with RecA protein in 10 mM Tris-acetate reaction buffer pH 7.5 at 37° C. RecA concentration during probe coating depended on the amount and size of the probe. The Mg acetate concentration was 2–20 mM and ATPγS (Pharmacia) was 0.49–4.8 mM. The resulting recA-DNA filaments are diluted in 20 mM HEPES buffer and 30 µg DOTAP N-[1–2,3-Dioleoyloxy)propyl]-N,N,N-trimethylammonium methylsulfate (Boehringer Mannheim) added in 100 µl of 20 mM HEPES buffer, incubated for 15 min at room temperature, and the resulting mixture added to the cells. The cells are incubated for 5 to 16h. β-gal plasmid is used as a control of the transfection efficiency. The pSVβ-Galactosidase Control Vector (Promega) was used as a positive control for monitoring transfection efficiency of Y1 cells. I n this vector the SV40 early promoter and enhancer unit drives transcription of the lacz gene which encodes the β-galactosidase enzyme. The pSV-β-Gal vector was co-transfected together with RecA coated DNA. Standard in situ β-Gal assay (Promega) was performed to determine transfection efficiency. The observed transfection efficiency is in excess of 90%. Cells are irradiated by light to crosslink coumarin. Changes in morphology and significant growth inhibition of the Y1 cells is observed upon treatment with the above-described nucleoproteins at a DNA concentration of 50 nM and higher.

II. Inhibition of Episomal Replication of the SV40 Origin.

COS-7 cells (Gluzman (1981) Cell 23:175–182) are used, which are characterized by having an integrated expression cassette providing constitutive expression of the large T antigen of SV40 with the SV40 early promoter.

Upon transfection into COS cells, plasmids containing the SV40 replication origin replicate efficiently in the nucleus as episomes.

In the following experiments for replication inhibition, the plasmid pSV2SPORT-1 (Life Technologies Mol. Cell. Biol. 2:1044–1051) is employed. This shuttle vector carries an SV40 origin, SV40 major early and late promoters and the transcriptional enhancer. In the experiments, several sequences are targeted in relation to the replication origin.

Plasmid pSV2SPORT-1 (Life Technologies) is transfected into COS-7 cells by the DEAE dextran method (McCutchan et al. (1968) Natl. Cancer Inst. Monogr.41:351–355) or electroporation. The nucleic acid sequences which are employed have the following sequences:
pair #1 (45bp) (SEQ ID No:1; SEQ ID No:2)
5'-CAGTTAGGGTGTGGAAAGTCCCCAGGCTCCCCA GCAGGCAGAAGT-3'
3'-GTCAATCCCACACCTTTCAGGGGTCCGAGGGGT CGTCCGTCTTCA-5'
pair #2 (45bp) (SEQ ID No:3; SEQ ID No:4)
5'-GAGTCGTATTATAAGCTAGCTTGGGATCTTTGTG AAGGAACCTTA-3'
3'-CTCAGCATAATATTCGATCGAACCCTAGAAACAC TTCCTTGGAAT-5'

Nucleoprotein filaments were prepared from these sequences as described above and introduced into the cells by lipofection as described above. Cells are irradiated by light to crosslink coumarin. The replication efficiency is then analyzed by first isolating autonomously replicating DNA by the standard Hirt procedure (Hirt (1967) J. Mol. Biol. 26: 365–369). To distinguish between replicated and non-replicated episomal DNA, the methylation sensitive restriction enzyme DpnI (Peden et al. (1980) Science 209:1392–1396) is employed. DpnI digests the GATC site only when the $^6$N-position of adenine is methylated on both DNA strands. The DNA that is used for transfection is cleaved by this enzyme. Conversely, DNA replicated at least once in mammalian cells lacking dam methylase will be DpnI resistant. The isolated DNA is digested with DpnI under conditions suggested by the supplier and the resulting fragments separated and resolved by agarose gel electrophoresis, blotted on nitrocellulose filters and hybridized with radiolabeled pSVSPORT-1. The amount of DpnI-resistant DNA over DpnI-sensitive DNA indicates the efficiency of episomal DNA replication. The replication of pSVSPORT-1 is inhibited more than 90% when the sequences are:
pair #1 (45bp) (SEQ ID No:1; SEQ ID No:2)
5'-CAGTTAGGGTGTGGAAAGTCCCCAGGCTCCCCA GCAGGCAGAAGT-3'
3'-GTCAATCCCACACCTTTCAGGGGTCCGAGGGGT CGTCCGTCTTCA-5'
pair #2 (45bp) (SEQ ID No:3; SEQ ID No:4)
5'-GAGTCGTATTATAAGCTAGCTTGGGATCTTTGTG AAGGAACCTTA-3'
3'-CTCAGCATAATATTCGATCGAACCCTAGAAACAC TTCCTTGGAAT-5' these sequences are for both sites in the replication origin. About 50% inhibition of replication is achieved when the targeted sequence is to either site of the origin of replication. These results are based on a comparison of the replication level where none of the above sequences are used or where nucleoprotein filaments comprising unrelated oligonucleotides are used.

To establish the relationship between termination sites and the targeted sequences, 2-D gel electrophoresis is used (Brinton et al. (1991) J. Biol. Chem. 266: 5153–5161). The termination sites within the replicative bubble are located at or near the sites targeted by the subject nucleoproteins.

It is evident from the above results that the subject method and compositions provide for a convenient and efficient way for modifying cells, where transcription can be inhibited. The modification may be temporary or permanent depending upon the nature of the nuclear proteins which are employed and the ancillary moieties which can act upon the target sequence. In this manner, cells may be modulated in culture and in vivo to allow for investigation of physiological processes, preparation of animal models, and therapeutic treatment of cells having an undesired phenotype.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of inhibiting copying of DNA at a target sequence in a viable cell, said method comprising:
introducing into said cell a pair of nucleoprotein filaments, wherein the nucleoprotein filaments comprise a ssDNA strand coated with a recombinase for insertion into dsDNA and a region of DNA homology with each other and with a target sequence in said cell; wherein said target sequence is a sequence of said gene;
whereby a double D-loop is formed and said copying is inhibited.

2. A method according to claim 1, wherein said target sequence is a gene.

3. A method according to claim 2, wherein said target sequence is proximal to or overlapping with a transcriptional regulatory sequence.

4. A method according to claim 1, wherein said region of DNA homology is at least 30 nt.

5. A method according to claim 3, wherein said ssDNA strand is at least 50 nt.

6. A method according to claim 1, wherein joined to at least one terminus of said ssDNA strand is a molecule that causes scission of dsDNA.

7. A method according to claim 1, wherein joined to at least one terminus of said ssDNA strand is a molecule capable of forming a covalent bond with ssDNA or dsDNA under intracellular conditions.

8. A method according to claim 1, wherein each of said pair of nucleoprotein filaments comprises first and second regions which are substantially contiguous when bound to said target sequence and wherein said first and second regions are joined by a ssDNA at a terminus of said first region to a terminus of said second region.

9. A method of inhibiting the transcription of a gene in a viable cell, said method comprising;
introducing by means of lipofection into said cell a pair of nucleoprotein filaments, wherein the nucleoprotein filaments comprise a ssDNA strand of at least 30 nt coated with a recombinase for insertion into dsDNA; and a region of DNA complementarity with each other and with a target sequence in said cell; wherein said target sequence is a sequence of said gene;
whereby a double D-loop is formed and said transcription is inhibited.

10. A method according to claim 9, wherein joined to at least one terminus of said ssDNA strand is a molecule that causes scission in dsDNA.

11. A method according to claim 10, wherein said molecule is a metal chelate.

12. A method according to claim 9, wherein joined to at least one terminus of said ssDNA strand is a molecule capable of forming a covalent bond with dsDNA under intracellular conditions.

13. A kit comprising a pair of nucleoprotein filaments comprising a ssDNA strand coated with a recombinase for insertion into dsDNA; wherein said filaments comprise first and second regions which are substantially contiguous when bound to a target sequence and wherein said first and second regions are joined at their termini by a ssDNA linker at a terminus of said first region to a terminus of said second region.

14. A kit according to claim 13 wherein at least one of said filaments is joined to a molecule that causes scission in dsDNA or forms a covalent bonds in ds or ssDNA under intracellular physiological conditions.

* * * * *

SEQUENCE LISTING

<160> NUMBER OF SEQ ID NOS: 4

<210> SEQ ID NO 1
<211> LENGTH: 45
<212> TYPE: DNA
<213> ORGANISM: Bacteria - plasmid pSV2SPORT-1

<400> SEQUENCE: 1
cagttagggt gtggaaagtc cccaggctcc ccagcaggca gaagt         45

<210> SEQ ID NO 2
<211> LENGTH: 45
<212> TYPE: DNA
<213> ORGANISM: Bacteria - plasmid pSV2SPORT-1

```
<400> SEQUENCE: 2
acttctgcct gctggggagc ctggggactt tccacaccct aactg                45

<210> SEQ ID NO 3
<211> LENGTH: 45
<212> TYPE: DNA
<213> ORGANISM: Bacteria - plasmid pSV2SPORT-1

<400> SEQUENCE: 3
gagtcgtatt ataagctagc ttgggatctt tgtgaaggaa cctta                45

<210> SEQ ID NO 4
<211> LENGTH: 45
<212> TYPE: DNA
<213> ORGANISM: Bacteria - plasmid pSV2SPORT-1

<400> SEQUENCE: 4
taaggttcct tcacaaagat cccaagctag cttataatac gactc                45
```